United States Patent
Novak, III et al.

(10) Patent No.: US 12,332,475 B2
(45) Date of Patent: *Jun. 17, 2025

(54) AEROSOL DELIVERY DEVICE

(71) Applicant: RAI STRATEGIC HOLDINGS, INC., Winston-Salem, NC (US)

(72) Inventors: Charles Jacob Novak, III, Winston-Salem, NC (US); Sean A. Daugherty, Yadkinville, NC (US); Michael Ryan Galloway, Winston-Salem, NC (US); Justin Holt, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/749,248

(22) Filed: Jun. 20, 2024

(65) Prior Publication Data

US 2024/0337788 A1    Oct. 10, 2024

Related U.S. Application Data

(63) Continuation of application No. 18/354,612, filed on Jul. 18, 2023, now Pat. No. 12,044,881, which is a
(Continued)

(51) Int. Cl.
*F21V 8/00*     (2006.01)
*A24F 40/50*    (2020.01)
(Continued)

(52) U.S. Cl.
CPC .............. *G02B 6/009* (2013.01); *A24F 40/50* (2020.01); *A24F 40/90* (2020.01); *A61M 11/041* (2013.01);
(Continued)

(58) Field of Classification Search
CPC .... G02B 6/009; G02B 6/0083; A61M 11/042; A61M 11/041; F21V 23/005;
(Continued)

(56) References Cited

U.S. PATENT DOCUMENTS 2,057,353 A    10/1936    Whittemore, Jr.
2,104,266 A     1/1938    McCormick
(Continued)

FOREIGN PATENT DOCUMENTS

CA    2922406    12/2014
CA    3048772     8/2018
(Continued)

OTHER PUBLICATIONS

International Search Report and Written Opinion issued in PCT/IB2019/059556 on Apr. 6, 2020.

*Primary Examiner* — Mary Ellen Bowman
(74) *Attorney, Agent, or Firm* — Womble Bond Dickinson (US) LLP

(57) ABSTRACT

The present disclosure provides an aerosol delivery device comprising a control device that is connectable with a cartridge and that can include one or more additional elements for improving one or both of visible indications of use to a user and resistance to infiltration of liquid into the control device. More particularly, the control device may include a light guide configured for transmitting to a window from a light source that is off-set from the window and a controller configured to direct a varying level of light from the light source. The control device may include one or more elements that are configured to limit infiltration of liquids into the control device and thus may be consider to be water-resistant or water-proof.

15 Claims, 7 Drawing Sheets

Related U.S. Application Data continuation of application No. 17/885,290, filed on Aug. 10, 2022, now Pat. No. 11,796,732, which is a continuation of application No. 17/483,424, filed on Sep. 23, 2021, now Pat. No. 11,460,631, which is a continuation of application No. 16/674,502, filed on Nov. 5, 2019, now Pat. No. 11,156,766.

(60) Provisional application No. 62/769,296, filed on Nov. 19, 2018.

(51) Int. Cl.
   *A24F 40/90* (2020.01)
   *A61M 11/04* (2006.01)
   *F21V 23/00* (2015.01)
   *F21Y 115/10* (2016.01)
   *G05B 19/042* (2006.01)
   *H02J 7/00* (2006.01)

(52) U.S. Cl.
   CPC ......... *A61M 11/042* (2014.02); *F21V 23/005* (2013.01); *G02B 6/0083* (2013.01); *G05B 19/042* (2013.01); *H02J 7/00* (2013.01); *H02J 7/0063* (2013.01); *H02J 7/007* (2013.01); *A61M 2205/3331* (2013.01); *A61M 2205/3576* (2013.01); *A61M 2205/50* (2013.01); *A61M 2205/587* (2013.01); *F21Y 2115/10* (2016.08); *G05B 2219/2639* (2013.01)

(58) Field of Classification Search
   CPC ........ G05B 19/042; H02J 7/00; H02J 7/0063; H02J 7/007
   See application file for complete search history.

(56) References Cited

U.S. PATENT DOCUMENTS

| | | | |
|---|---|---|---|
| 3,200,819 A | 8/1965 | Gilbert | |
| 4,922,901 A | 5/1990 | Brooks et al. | |
| 5,060,671 A | 10/1991 | Counts et al. | |
| 5,093,894 A | 3/1992 | Deevi et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 8,528,569 B1 | 9/2013 | Newton | |
| 8,833,364 B2 | 9/2014 | Buchberger | |
| 9,078,472 B2 | 7/2015 | Liu | |
| 9,220,304 B2 | 12/2015 | Greim | |
| 9,462,831 B2 | 10/2016 | Liu | |
| 9,532,605 B2 | 1/2017 | Yamada et al. | |
| 9,877,508 B2 | 1/2018 | Kane | |
| 9,949,510 B2 | 4/2018 | Liu | |
| 9,974,338 B2 | 5/2018 | Alarcon et al. | |
| 10,015,990 B2 | 7/2018 | Mironov | |
| 10,028,537 B1 | 7/2018 | Hawes et al. | |
| 10,058,125 B2 | 8/2018 | Worm et al. | |
| 10,080,851 B2 | 9/2018 | Davidson et al. | |
| 10,085,481 B2 | 10/2018 | Verleur et al. | |
| 10,092,037 B2 | 10/2018 | Tucker et al. | |
| 10,104,913 B2 | 10/2018 | Lau et al. | |
| 10,117,463 B2 | 11/2018 | Thomas | |
| 10,117,467 B2 | 11/2018 | Hawes et al. | |
| 10,492,529 B2 | 12/2019 | Borkovec et al. | |
| 11,156,766 B2 * | 10/2021 | Novak, III ........... G05B 19/042 |
| 11,311,688 B2 | 4/2022 | Phillips et al. | |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0151717 A1 | 6/2009 | Bowen et al. | |
| 2009/0188490 A1 | 7/2009 | Hon | |
| 2009/0272379 A1 | 11/2009 | Thorens et al. | |
| 2009/0320863 A1 | 12/2009 | Fernando et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2013/0037041 A1 | 2/2013 | Worm et al. | |
| 2013/0042865 A1 | 2/2013 | Monsees et al. | |
| 2013/0306084 A1 | 11/2013 | Flick | |
| 2013/0319435 A1 | 12/2013 | Flick | |
| 2014/0000638 A1 | 1/2014 | Sebastian et al. | |
| 2014/0007892 A1 | 1/2014 | Liu | |
| 2014/0096781 A1 | 4/2014 | Sears et al. | |
| 2014/0096782 A1 | 4/2014 | Ampolini et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0366898 A1 | 12/2014 | Monsees et al. | |
| 2015/0020831 A1 | 1/2015 | Weigensberg et al. | |
| 2015/0020832 A1 | 1/2015 | Greim et al. | |
| 2015/0027471 A1 | 1/2015 | Feldman et al. | |
| 2015/0150308 A1 | 6/2015 | Monsees et al. | |
| 2015/0164142 A1 | 6/2015 | Li et al. | |
| 2015/0208729 A1 | 7/2015 | Monsees et al. | |
| 2015/0282527 A1 | 10/2015 | Henry, Jr. | |
| 2015/0296888 A1 | 10/2015 | Liu | |
| 2015/0313287 A1 | 11/2015 | Verleur et al. | |
| 2016/0091194 A1 | 3/2016 | Liu | |
| 2016/0262453 A1 | 9/2016 | Ampolini et al. | |
| 2017/0027226 A1 | 2/2017 | Mironov et al. | |
| 2017/0071256 A1 | 3/2017 | Verleur et al. | |
| 2017/0095005 A1 | 4/2017 | Monsees et al. | |
| 2017/0112191 A1 | 4/2017 | Sur et al. | |
| 2017/0135404 A1 | 5/2017 | Reevell | |
| 2017/0135405 A1 | 5/2017 | Reevell | |
| 2017/0143042 A1 | 5/2017 | Batista et al. | |
| 2017/0196263 A1 | 7/2017 | Sur | |
| 2017/0215485 A1 | 8/2017 | Zitzke | |
| 2017/0231281 A1 | 8/2017 | Hatton et al. | |
| 2017/0231282 A1 | 8/2017 | Hatton et al. | |
| 2017/0325289 A1 | 11/2017 | Liu | |
| 2017/0340011 A1 | 11/2017 | Batista | |
| 2017/0340012 A1 | 11/2017 | Mironov et al. | |
| 2017/0347706 A1 | 12/2017 | Aoun et al. | |
| 2017/0347711 A1 | 12/2017 | Litten et al. | |
| 2017/0347712 A1 | 12/2017 | Singh | |
| 2018/0000157 A1 | 1/2018 | Batista et al. | |
| 2018/0000160 A1 | 1/2018 | Taschner et al. | |
| 2018/0014575 A1 | 1/2018 | Fursa | |
| 2018/0020721 A1 | 1/2018 | Garthaffner et al. | |
| 2018/0020725 A1 | 1/2018 | Alarcon et al. | |
| 2018/0020727 A1 | 1/2018 | Hoffman et al. | |
| 2018/0020731 A1 | 1/2018 | Rasmussen et al. | |
| 2018/0020734 A1 | 1/2018 | Angstead et al. | |
| 2018/0020736 A1 | 1/2018 | Silvestrini | |
| 2018/0027878 A1 | 2/2018 | Dendy et al. | |
| 2018/0035717 A1 | 2/2018 | Batista | |
| 2018/0042306 A1 | 2/2018 | Atkins et al. | |
| 2018/0043114 A1 | 2/2018 | Bowen et al. | |
| 2018/0077967 A1 | 3/2018 | Hatton et al. | |
| 2018/0084831 A1 | 3/2018 | Mironov | |
| 2018/0103685 A1 | 4/2018 | Yener | |
| 2018/0132525 A1 | 5/2018 | Patil et al. | |
| 2018/0140009 A1 | 5/2018 | Sur et al. | |
| 2018/0140019 A1 | 5/2018 | Guo et al. | |
| 2018/0161525 A1 | 6/2018 | Liu et al. | |
| 2018/0177230 A1 | 6/2018 | Hawes et al. | |
| 2018/0198297 A1 | 7/2018 | Grzan et al. | |
| 2018/0213850 A1 | 8/2018 | Brinkley et al. | |
| 2018/0242643 A1 | 8/2018 | Silvestrini et al. | |
| 2018/0280637 A1 | 10/2018 | Mayle et al. | |
| 2018/0295882 A1 | 10/2018 | Ricketts et al. | |
| 2018/0295888 A1 | 10/2018 | Newcomb et al. | |

(56) References Cited

U.S. PATENT DOCUMENTS

| | | |
|---|---|---|
| 2018/0296777 A1 | 10/2018 | Terry et al. |
| 2018/0303160 A1 | 10/2018 | Davis et al. |
| 2018/0310616 A1 | 11/2018 | Clemens et al. |
| 2018/0352608 A1 | 12/2018 | Shoched |
| 2019/0387797 A1 | 12/2019 | Christensen et al. |
| 2020/0000146 A1 | 1/2020 | Anderson et al. |
| 2020/0119489 A1 | 4/2020 | Novak |

FOREIGN PATENT DOCUMENTS

| | | |
|---|---|---|
| CN | 1541577 | 11/2004 |
| CN | 2719043 | 8/2005 |
| CN | 201379072 | 1/2010 |
| CN | 103948177 | 7/2014 |
| CN | 203897292 | 10/2014 |
| CN | 108025149 A | 5/2018 |
| CN | 108471806 A | 8/2018 |
| CN | 108697161 A | 10/2018 |
| EP | 1 618 803 | 1/2006 |
| EP | 2654469 | 10/2013 |
| EP | 3275319 | 1/2018 |
| WO | WO 2004/080216 | 9/2004 |
| WO | WO 2005/099494 | 10/2005 |
| WO | WO 2007/131449 | 11/2007 |
| WO | WO 2014/199233 | 12/2014 |
| WO | WO 2015/035510 | 3/2015 |
| WO | WO 2016/026811 | 2/2016 |
| WO | WO 2016/124717 | 8/2016 |
| WO | WO 2017/051006 | 9/2016 |
| WO | WO 2017/207442 | 5/2017 |
| WO | WO 2018/163261 | 9/2018 |
| WO | WO 2018/167166 | 9/2018 |
| WO | WO 2018/202732 | 11/2018 |

\* cited by examiner

AEROSOL DELIVERY DEVICE

CROSS-REFERENCE TO RELATED APPLICATIONS

This application is a continuation of U.S. application Ser. No. 18/354,612, filed Jul. 18, 2023, which is a continuation of U.S. patent application Ser. No. 17/885,290, filed on Aug. 10, 2022 (now U.S. Pat. No. 11,796,732), which is a continuation of U.S. patent application Ser. No. 17/483,424, filed Sep. 23, 2021 (now U.S. Pat. No. 11,460,631), which is a continuation of U.S. patent application Ser. No. 16/674,502, filed Nov. 5, 2019 (now U.S. Pat. No. 11,156,766), which claims priority to U.S. Provisional Patent Application No. 62/769,296, filed Nov. 19, 2018, which are incorporated herein in their entirety by reference.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety. It would be desirable to provide an aerosol delivery device with advantageous usability features.

BRIEF SUMMARY

The present disclosure relates to aerosol delivery devices, methods of forming such devices, and elements of such devices. In particular, the present disclosure relates to various elements and combinations thereof that are effective to provide one or more a more favorable user experience of the devices and improved resistance of the devices to liquid infiltration. For example, in some embodiments, the present disclosure provides aerosol delivery devices that can provide lighting that is visible exterior to the device (e.g., through an aperture or a series of micro-apertures in the device). Likewise, in some embodiments, the present disclosure can provide devices that include one or more features (e.g., sealing members or micro-sized apertures) that can improve water resistance of the device.

In one or more embodiments, the present disclosure thus can provide an aerosol delivery device comprising: at least one wall defining an outer housing; a window in the at least one wall, the window extending between a first end and a second end; a light source positioned within the outer housing and proximate the window but offset therefrom so as to be beyond one of the first end of the window and the second end of the window, the light source being connectable to a power source; a light guide positioned within the outer housing and proximate the window, the light guide being of sufficient size to substantially fill the window and at least partially overlap with the light source; and a control component configured to direct power at a variable level from the power source to the light source such that light emitted from the light source is transmitted through the light guide and fills a quantity of the window, the quantity corresponding to the variable level of power delivered to the light source. In further embodiments, the aerosol delivery device can be defined in relation to one or more of the following statements, which can be combined in any number and order.

The position of the light source and the position of the light guide can be effective to achieve the light emitted from the light source and transmitted through the light guide to grow in a direction from one of the first end of the window and the second end of the window to the other of the first end of the window and the second end of the window as power delivered from the power source to the light source increases and to recede in reverse of the direction as power delivered from the power source to the light source decreases.

The aerosol delivery device further can include a pressure sensor configured to detect changes in pressure within the outer housing across a continuous pressure intensity range and provide signaling to the controller corresponding to the pressure intensity.

The control component can be configured to adjust the variable level of the power delivered from the power source to the light source in response to the signaling received from the pressure sensor.

The power source and the control component can be configured for connection with an atomizer.

The control component can be configured to direct power at a variable level from the power source to the atomizer in response to the signaling received from the pressure sensor.

The aerosol delivery device further can comprise a printed circuit board positioned within the outer housing, the light source being positioned on the printed circuit board.

The control component can be positioned on the same printed circuit board as the light source.

The aerosol delivery device further can comprise a sealing member positioned between the light guide and the at least one wall defining the outer housing.

The sealing member can be integral with the light guide.

The light guide can be formed of a translucent elastomeric material.

The aerosol delivery device further can comprise a liquid-resistive membrane positioned interior to the outer housing, the liquid-resistive membrane covering the window in the at least one wall.

The liquid-resistive membrane can be adhered to an interior surface of the at least one wall.

In some embodiments, an aerosol delivery device can be provided comprising: at least one wall defining an outer housing extending between a proximal end and a distal end; an inner frame positioned within the outer housing at the proximal end thereof and defining a chamber configured for receiving a cartridge; an end cap positioned at the distal end of the outer housing; and at least one sealing member in contact with the inner frame or the end cap and being configured to substantially prevent passage of a liquid around the at least one sealing member. In further embodiments, the aerosol delivery device can be defined in relation to one or more of the following statements, which can be combined in any number and order The at least one sealing member can comprise an O-ring.

The O-ring can be positioned between the inner frame and the at least one wall defining the outer housing.

The inner frame can include a groove formed around an outer surface thereof, and wherein the O-ring is engaging the groove.

The O-ring can be positioned between the end cap and the at least one wall defining the outer housing.

The end cap can include a groove formed around an outer surface thereof, and wherein the O-ring is engaging the groove.

The at least one sealing member can comprise a contact seal configured to form a seal between the inner frame and one or more electrical connectors extending through the inner frame.

The at least one sealing member can comprise a pin seal configured to form a seal between the end cap and one or more external connection elements extending through the end cap.

The at least one sealing member can comprise a sensor seal that is substantially surrounding a pressure sensor attached to a printed circuit board.

The sensor seal can include a flexible member that is configured to deform upon application of a pressure differential thereto.

The sensor seal can be configured to define an enclosed volume around the pressure sensor and transfer the pressure differential to the pressure sensor.

In some embodiments, an aerosol delivery device can be provided comprising: at least one wall defining an outer housing; and a light source positioned interior to the housing; wherein at least a portion of the at least one wall includes a series of microperforations; and wherein the light source is positioned relative to the series of microperforations such that light from the light source is visible through the series of microperforations. In further embodiments, the aerosol delivery device can be defined in relation to one or more of the following statements, which can be combined in any number and order.

The light source can be off-set from the series of perforations, and wherein the aerosol delivery device further can comprise a light guide positioned within the outer housing, the light guide being proximate to the series of microperforations and at least partially overlapping with the light source.

The at least one wall defining the outer housing can extend between a proximal end and a distal end, and wherein the aerosol delivery device further can comprise: an inner frame positioned within the outer housing at the proximal end thereof and defining a chamber configured for receiving a cartridge; an end cap positioned at the distal end of the outer housing; and at least one sealing member in contact with the inner frame or the end cap and being configured to substantially prevent passage of a liquid around the at least one sealing member.

BRIEF DESCRIPTION OF THE FIGURES

Figure 1:
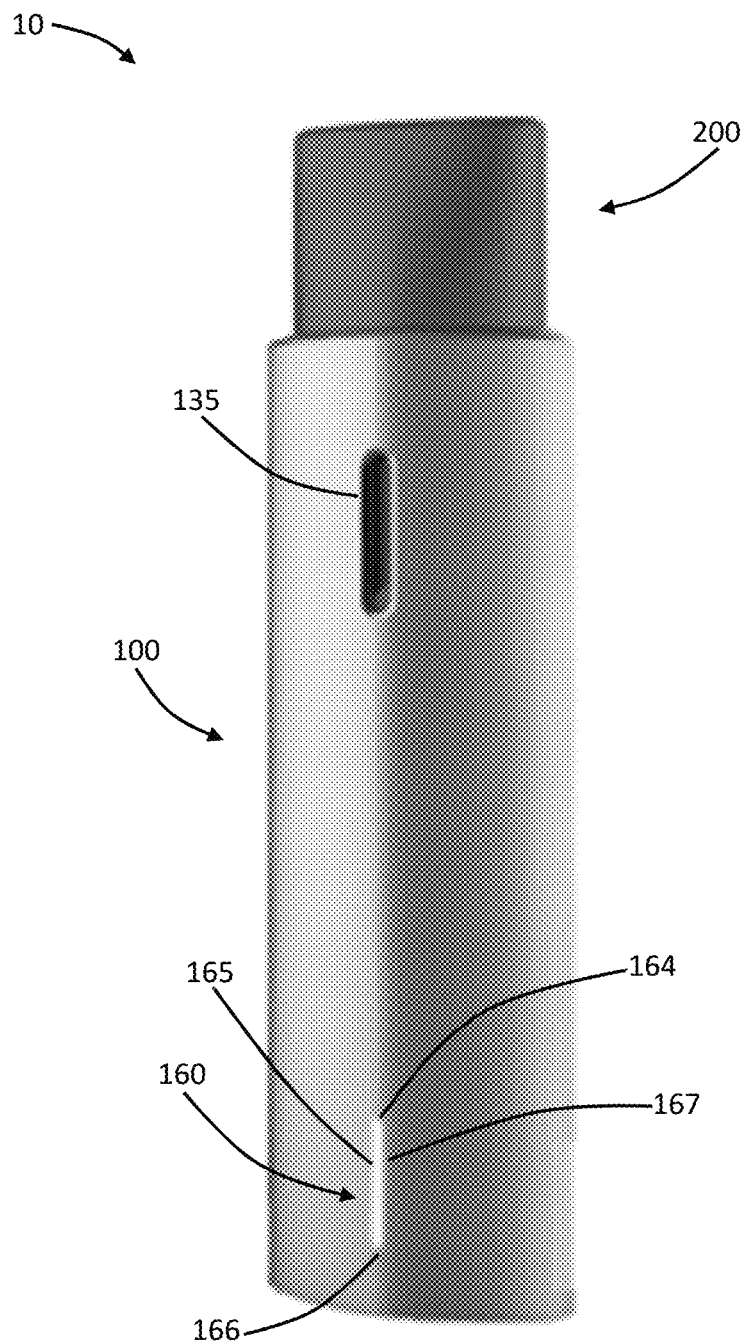
Figure 2:
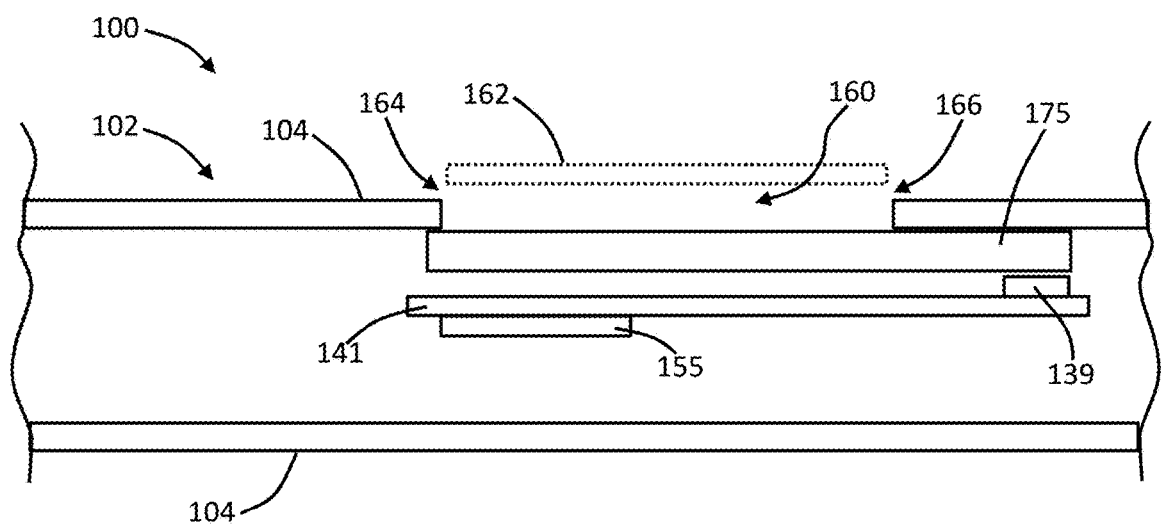
Figures 3A, 3B, 3C, 3D:
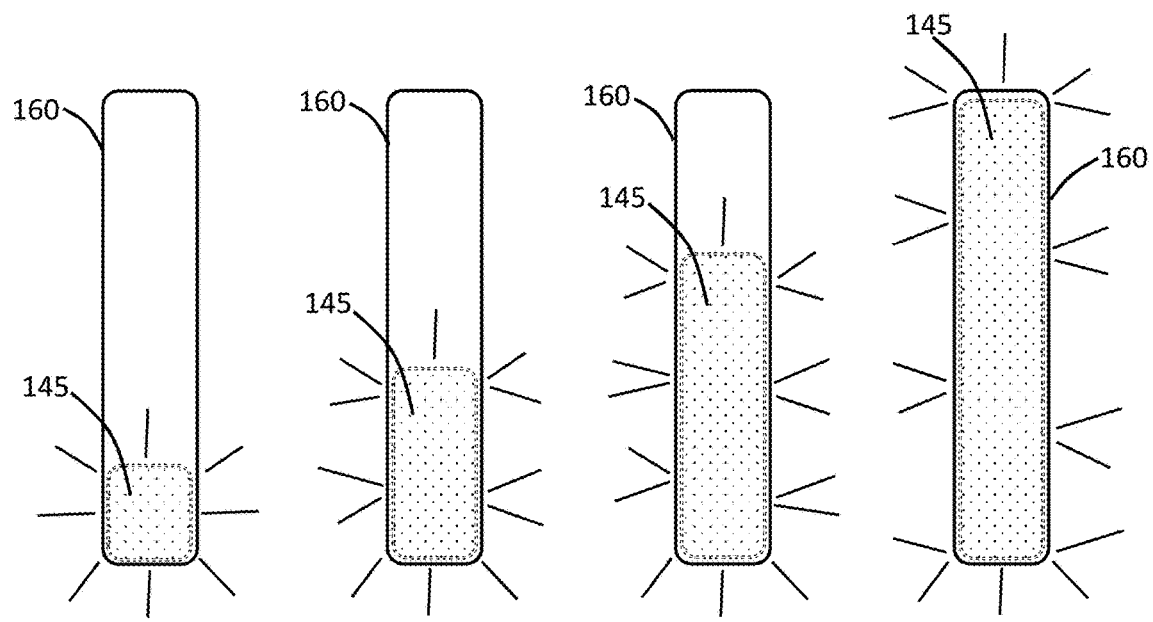
Figure 4:
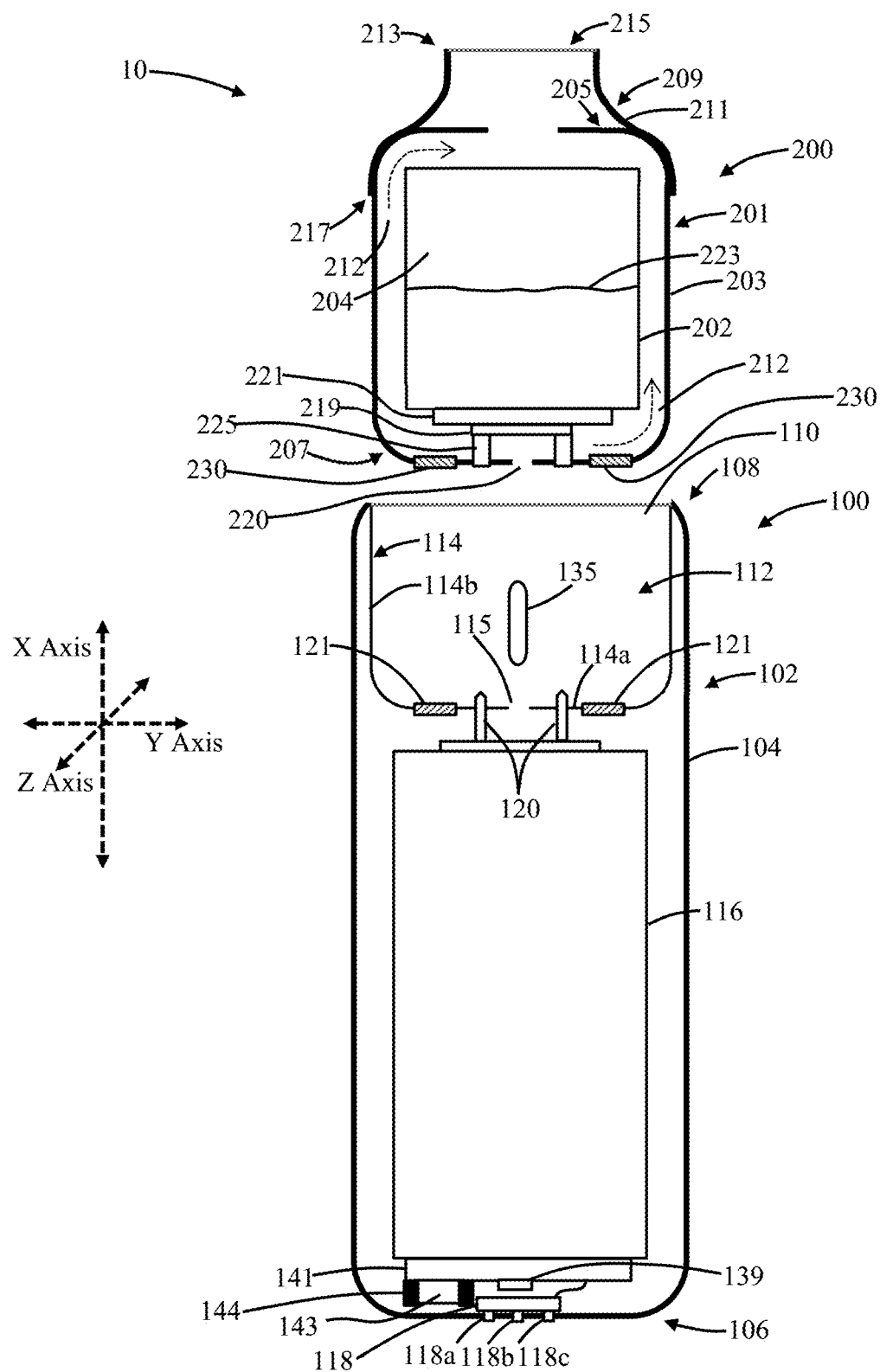
Figure 5:
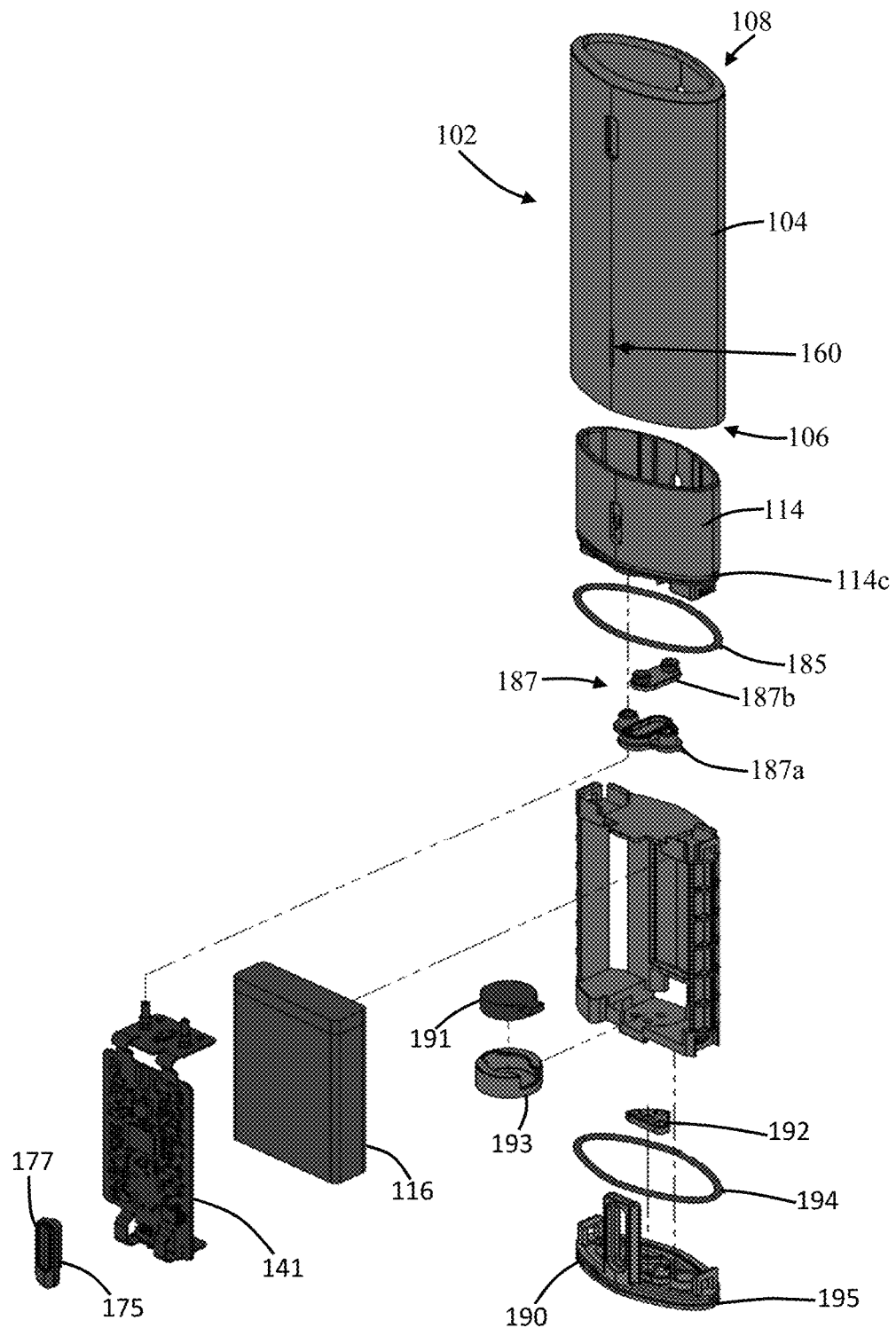
Figure 6:
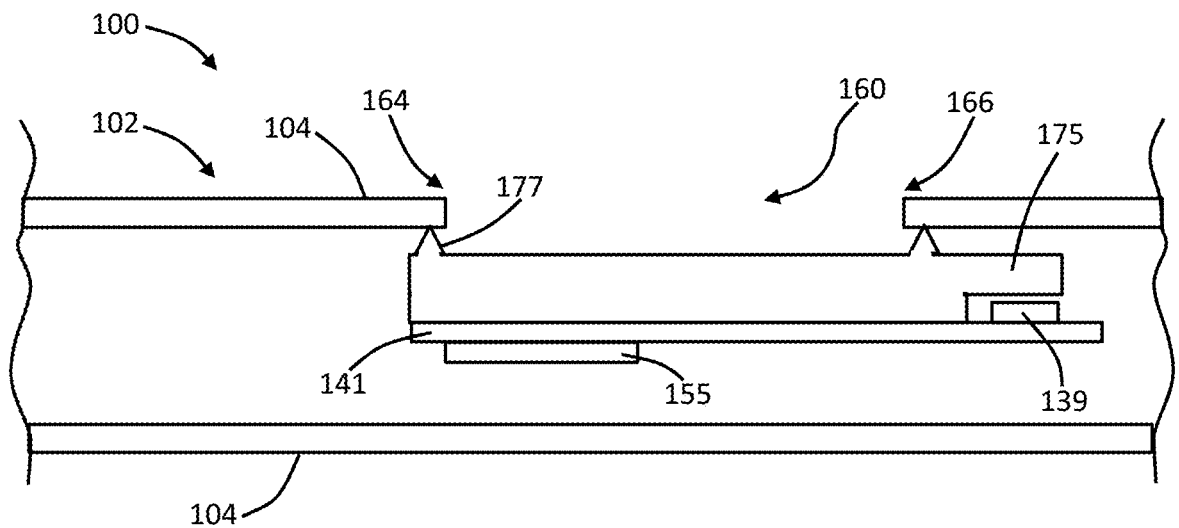
Figure 7:
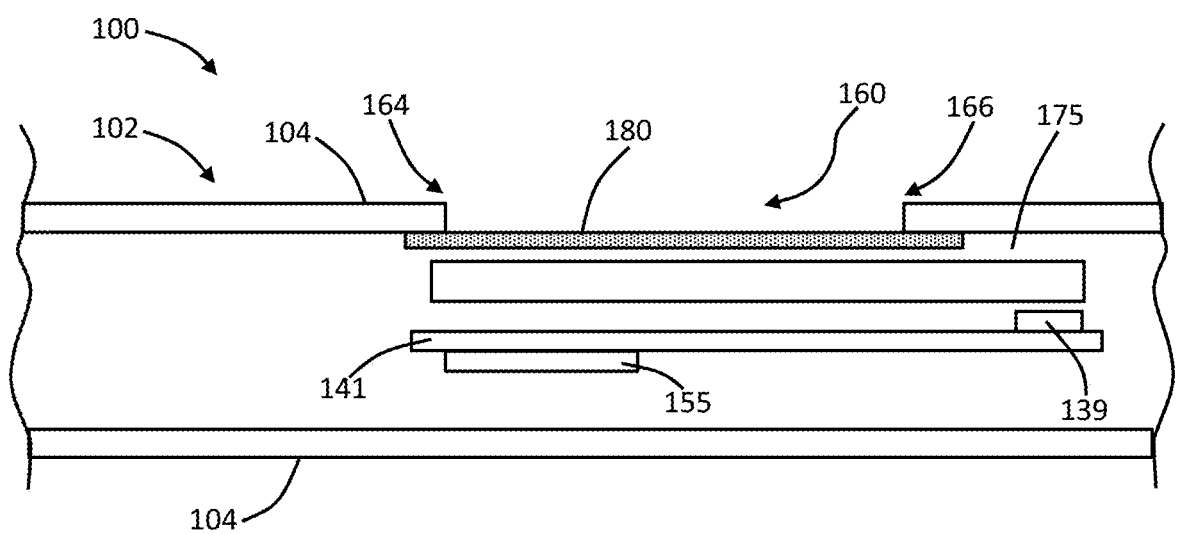
Figure 8:
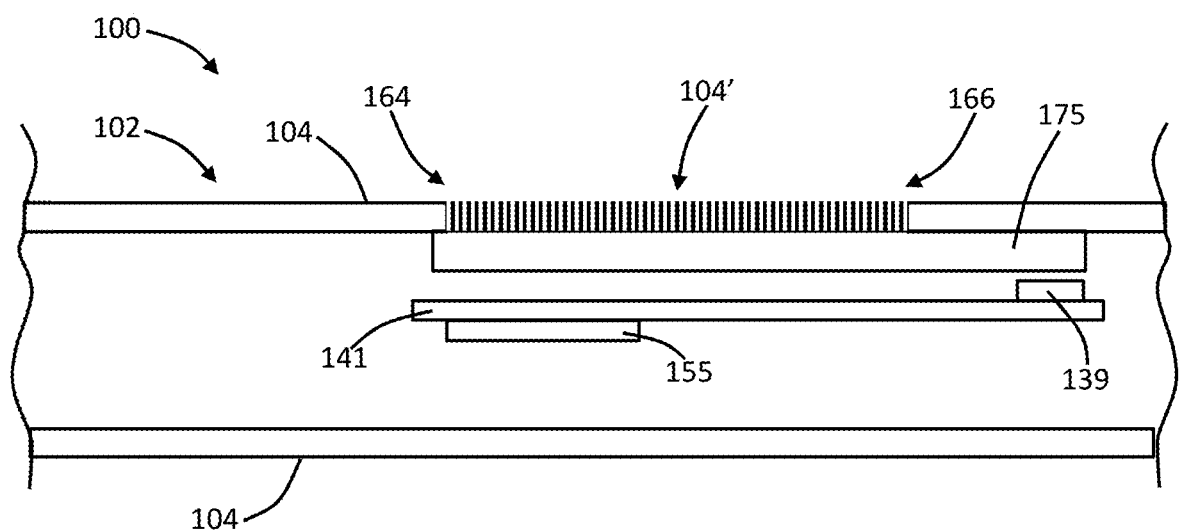
Figure 9:
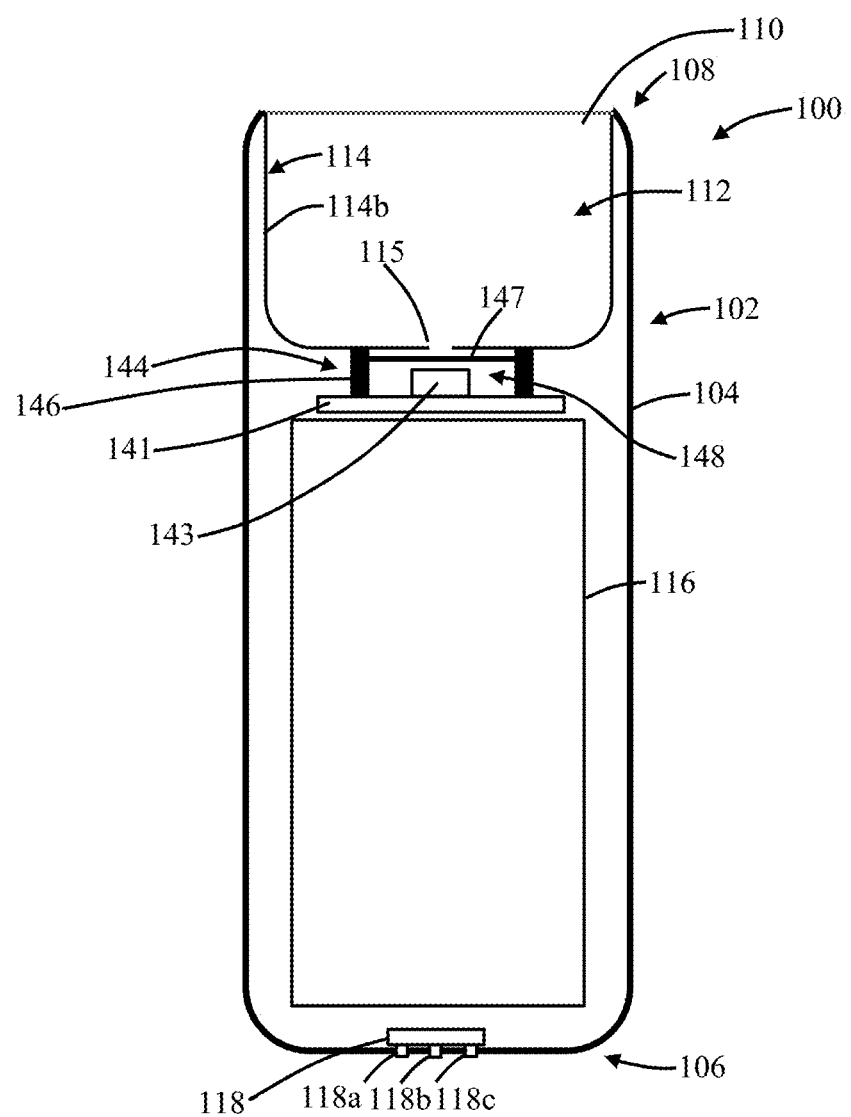

Having thus described the disclosure in the foregoing general terms, reference will now be made to the accompanying drawings, which are not necessarily drawn to scale, and wherein:

FIG. 1 is a perspective view of an aerosol delivery device, according to example implementations of the present disclosure;

FIG. 2 is a partial cross-sectional view of a portion of a control device illustrating implementation of a light guide proximate to a light window according to example embodiments of the present disclosure;

FIG. 3A, FIG. 3B, FIG. 3C, and FIG. 3D illustrate a growing light effect as light from a light source progressively fills a light window according to example embodiments of the present disclosure;

FIG. 4 is a partial cross-sectional view of an aerosol delivery device including a control device and a cartridge according to example embodiments of the present disclosure;

FIG. 5 is an exploded view of a control device including elements useful for providing resistance to liquid infiltration;

FIG. 6 is a partial cross-sectional view of a portion of a control device illustrating implementation of a light guide proximate to a light window according to example embodiments of the present disclosure;

FIG. 7 is a partial cross-sectional view of a portion of a control device illustrating implementation of a light guide and a sealing member proximate to a light window according to example embodiments of the present disclosure;

FIG. 8 is a partial cross-sectional view of a portion of a control device illustrating implementation of a light guide proximate to a portion of a wall of the control device including micro-perforations according to example embodiments of the present disclosure; and FIG. 9 is a partial cross-sectional view of a control device illustrating implementation of a sensor seal around a pressure sensor according to example embodiments of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize and/or aerosolize a material to form an inhalable substance; and components of such devices have the form of articles that most preferably are sufficiently compact to be considered hand-held devices. In some embodiments, the present aerosol delivery devices may be configured to heat a material (preferably without combusting the material to any significant degree and/or without significant chemical alteration of the material) to form the inhalable substance. Preferably, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), a heater or heat generation member (e.g., an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

In some embodiments, the presently disclosed subject matter may be used in relation to a variety of aerosol and/or vapor producing devices. This includes, but is not limited to devices commonly known as e-cigarettes, heat-not-burn (HNB) devices, carbon tobacco heated products (cTHP), and electric tobacco heated products (cTHP). Non-limiting examples of such devices to which any part or all of the present disclosure may be incorporated are described in U.S. Pat. Nos. 9,839,238, 9,913,493, 10,085,485, More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

An example implementation of an aerosol delivery device 10 of the present disclosure is shown in FIG. 1. As illustrated, an aerosol delivery device 10 can comprise a control device 100 and a removable cartridge 200. As further described elsewhere herein, the control device 100 can be adapted to or configured to receive a portion of the cartridge 200, the combination of the cartridge and the control device 100 forming a functioning device. The control device 100 may include an aperture 135 (e.g., a cut-out, opening, or notch) to allow for viewing of the cartridge 100 when inserted into the control device; however, the window 135 may be expressly excluded. The control device 100 further includes a light window 160 that can be adapted to or configured to provide exterior viewing of a variable intensity light provided therethrough. Electronic circuitry present in the aerosol delivery device 10 can be configured to control the transmission of lighting through the light window 160 to provide one or more effects visible by a user of the device. For example, the lighting can provide feedback to a user for a variable puff draw intensity and corresponding power level indication. In particular, this can be achieved using one or more light emitting diode (LED) so as to produce a variable illumination intensity window.

In some embodiments, an aerosol delivery device 10 according to the present disclosure can be configured substantially as illustrated in FIG. 2, which provides a partial cross sectional view of a portion of a control device 100 comprising an outer housing 102 that defined at least in part by a control device outer wall 104. In the illustrated embodiments, a light window 160 is defined in the outer wall 104 and extends along a direction parallel to the longitudinal axis of the control device 100 between a first window end 164 and a second window end 166. The light window 160 of the illustrated embodiment likewise extends along a direction perpendicular to the longitudinal axis of the control device 100 between a first side 165 and a second side 167. The light window 160 may be essentially a cut-out or aperture present within the outer wall 104. More particularly, the light window 160 can comprise a slot, cut out, cut away, or any other method to expose an opening into the internal components. In some embodiments, however, the light window may be at least partially filled or completely filled with a transparent or translucent member 162 (as illustrated in FIG. 2 by the partially removed element shown in dashed lines). The transparent or translucent member 162 may be formed, for example, of glass, plastic, or similar materials. The light window 160 in some embodiments is greater in length in the direction between the first end 164 and the second end 166 than in the direction between the first side 165 and the second side 167. The ratio of the end-to-end length to the side-to-side length can be, for example, about 1.5 to about 15, about 2 to about 12, or about 3 to about 10. In some embodiments, the light window 160 may encompass a defined area of the control device outer housing 102, and the defined area can be an area encompassing at least 5 mm$^2$, at least 10 mm$^2$, or at least 20 mm$^2$ (such as in the range of about 5 mm$^2$ to about 50 mm$^2$, about 5 mm$^2$ to about 40 mm$^2$, or about 5 mm$^2$ to about 25 mm$^2$).

As further seen in FIG. 2, a light source 139 is positioned within the outer housing 102. As illustrated, the light source 139 is positioned proximate to the light window 160. Any element configured for emitting light may be used as the light source 139 and, in some embodiments, the light source particularly can be a light emitting diode (LED). While only a single LED or like element may be used, multiple light elements configured for emitting light of the same or different color may be used.

In the illustrated embodiment, the light source 139 is positioned so as to be offset from the light window 160—i.e., it is positioned beyond one of the first end 164 and the second end 166 of the light window. While the light source 139 is illustrated as being offset so as to be beyond the second end 166 of the light window 160, it is understood that the light source may be offset so as to be beyond the first end 164 of the light window. In either case, the light source 139 of such embodiments is not positioned within the actual boundaries of the light window 160 and, as such, is not positioned so as to be capable of providing significant light distribution through the light window. More particularly, offset placement of the light source 139 can be configured so that the light source is placed in a manner such that the location of the light source is not directly pointed at the light window 160.

The offset positioning of the light source 139, however, positions the light source to provide a varying intensity of light through the light window 160 by use of the light guide 175. More particularly, the light guide 175 is positioned within the outer housing 102, is positioned proximate to the light window 160, and is of a sufficient size to substantially fill the light window and at least partially overlap with the light source 139. As illustrated, the light guide 175 extends from beyond the second end 166 of the light window 160 to beyond the first end 164 of the light window. Preferably, the light guide 175 is similarly sized in relation to the side-to-side dimensions of the light window 160. The light guide 175 can be any light conductive-type materials that is adapted to or configured to conduct light from the light source 139 so as to partially fill the light window 160 in some embodiments and completely fill the light window in some embodiments. For example, light guide 175 can comprise light pipes, silicon, plastic, or any other semi-translucent material that allows the conduction of light therethrough. As non-limiting example embodiments, a suitable light guide 175 may be at least partially formed of a transparent or translucent material that may include one or more additives adapted to or configured to aid in the desired diffusion, refraction, reflection, and/or attenuation of the light as it passes through the material longitudinally, to enhance the desired growing effect. Non-limiting examples include inclusion of glass and/or pigment or other solid particles in a polymer. These particles may be used to enhance the diffusion of the light moving substantially down the light pipe longitudinally, the particles reflecting or refracting a portion of the light in a different direction that allows it to exit the opening in the housing. The remaining amount of light that continues moving down the light pipe longitudinally is continuously attenuated by the amount absorbed or reflected/refracted/diffused in a direction to exit the opening in the housing, thereby creating an effect where the light pipe emits less light in the direction to exit the opening in the housing at the end of the opening distant from the light source, while allowing more light to exit the opening at the end closest to the light source.

In some embodiments, the light guide 175 may utilize geometry such as included angled surfaces and selectively applied gloss and/or matte finishes, to assist in changing the direction of the of light in the desired manner to create a growing effect in the light window 160. It is the intentional attenuation of the light as it moves down the light guide 175 longitudinally and the gradient of intensity as it is emitted from the close or far end from the light source at a given light intensity level that can be particularly useful for providing a growing effect in the light window 160.

In the embodiment illustrated in FIG. 2, the light source 139 is positioned proximate to the light window 160; however, it is understood that the light source may be positioned a further distance from the light window. In such embodiments, the light guide 175 may be simply enlarged so as to extend a suitable distance to at least partially overlap with the light source 139 and also cover the light window 160 as discussed above. In other embodiments, a plurality of separate light guides 175 may be utilized. For example, a first light guide may be as substantially illustrated in FIG. 2 and may extend from the light source 139 toward the light window 160 but not covering the light window, and a second light guide may be as substantially illustrated in FIG. 5 and may partially or completely cover the light window and extend toward the first light guide. The first light guide and the second light guide (i.e., the plurality of light guides 175) may then be in a sufficient relationship so that light from the light source 139 is transmitted through the plurality of light guides to the light window 160 as otherwise described herein.

The aerosol delivery device further includes one or more control components. As seen in FIG. 2, the control component 141 is positioned on the same printed circuit board (PCB) as the light source 139. It is understood, however, that the control component 141 may be on a separate PCB. The control component 141 can be adapted to or configured to cause the light source 139 to emit light at different light intensities so that the light transmitted through the light guide 175 fills a portion of the light window 160 or substantially completely fills the light window. For example, the control component 141 may be configured to direct power at a variable level from a power source to the light source 139 such that light emitted from the light source is transmitted through the light guide 175 and fills a quantity of the light window 160, the quantity corresponding to the variable level of power delivered to the light source. This variable filling of light 145 in the light window 160 is illustrated in FIG. 3A through FIG. 3D. By varying the light intensity of light 145 visible through the light window 165 as emitted through the light guide 175, the aerosol delivery device can be configured to create a growing light effect that can provide feedback to the user as to how hard they are drawing on the device, as detected by a pressure sensor 143, as well as a power level of the device being dictated by the draw level reading of the pressure sensor. The controller of such embodiments will read input information from the pressure sensor, and the controller will output the appropriate power level to the heater. The controller 155 of some embodiments thus can output a corresponding intensity level to the light source 139 based on a pressure sensor reading in one or more embodiments. The pressure sensor can be configured to detect changes in pressure within the outer housing across a continuous pressure intensity range and provide signaling to the controller corresponding to the pressure intensity.

Although the variable filling of light 145 in the light window 160 is discussed above in relation to showing the draw intensity on the device, it is understood that this is providing an example embodiment for ease of understanding of how the controller can control the light intensity in the light window. The variable filling of light 145 in the light window 160 can be embodied in relation to any function of the device. For example, the variable filling of light 145 in the light window 160 can indicate a real-time battery level of a battery in the device such that the amount of light filling the light window can decrease as the battery charge decreases. As a further example, the variable filling of light 145 can be shown during charging of a battery of the device. In particular, the light intensity or the amount of the light window 160 filled with light 145 can increase as the battery charges such that a fully illuminated light window can be indicative of a fully charged battery. Likewise, the controller may be adapted to or configured to directly measure and/or estimate an amount of e-liquid remaining in a cartridge of the device. The controller may then control an amount of light 145 filling the light window 160 to substantially or approximately correspond to the amount of e-liquid remaining in an attached cartridge (e.g., the light window may be fully illuminated when a new cartridge is attached, and the amount of light 145 shining through the light window 160 may decrease as the e-liquid is depleted through use of the device). Even further functions or statuses of the device may be illustrated through the variable filling of the light window 160 with light 145.

The position of the light source 139 and the position of the light guide 175 can be effective to achieve the light 145 emitted from the light source and transmitted through the light guide to grow in a direction from one of the first end 164 of the window 160 and the second end 166 of the window to the other of the first end of the window and the second end of the window as power delivered from the power source to the light source increases and to recede in reverse of the direction as power delivered from the power source to the light source decreases. The control component 155 thus can be configured to adjust a variable level of power delivered from a power source to the light source 139 in response to signaling received from the pressure sensor 143. The pressure sensor can comprise any means by which to detect a pressure differential on the device upon the user drawing on the device such as microphone, barometric pressure senor, or any other method to be able to detect the change in airflow throughout the device. Power level control can be achieved by using the feedback from the pressure sensor, a microprocessor, SOC, or another controller can then adjust the power level being supplied to the heater by adjusting, for example, the voltage, current, PWM, or total power.

The aerosol delivery device 10 can include a variety of further components as illustrated in FIG. 4. Similar to as described above, the aerosol delivery device 10 can comprise a control device 100 and a cartridge 200 (or cartomizer). The cartridge 200 is engagable with the control device 100 to form an operating aerosol delivery device, and the cartridge is removable therefrom.

The control device can comprise an outer housing 102 that defines a control device outer wall 104, a control device distal end 106, and a control device proximal end 108. The control device proximal end 108 includes an opening 110 that provides access to a control device chamber 112 that is defined by a control device inner frame 114. In some embodiments, the control device inner frame 114 may include an aperture 115 that can be configured for transferring pressure differentials therethrough to a sensor 143 positioned within the control device 100 when air is drawn into the control device chamber 112. As illustrated, the sensor 143 is positioned on a printed circuit board (PCB). Configurations of a PCB and a pressure sensor, for example, are described in U.S. Pat. Pub. No. 2015/0245658 to Worm et al., the disclosure of which is incorporated herein by reference. The sensor 143 can be positioned anywhere within the control device 100 so as to subject to airflow and/or a pressure change that can signal a draw on the device and thus cause the battery 116 to delivery power to the heater 219 in the cartridge 200. Alternatively, in the absence of an airflow sensor, the heater 219 may be activated manually, such as by a push button. Additional representative types of sensing or detection mechanisms, structure and configuration thereof, components thereof, and general methods of operation thereof, are described in U.S. Pat. No. 5,261,424 to Sprinkel, Jr.; 5,372,148 to McCafferty et al.; and PCT WO 2010/003480 to Flick; which are incorporated herein by reference.

The control device 100 further can include a battery 116 positioned within the control device outer housing 102. Examples of batteries that can be used according to the disclosure are described in U.S. Pat. Pub. No. 2010/0028766 to Peckerar et al., the disclosure of which is incorporated herein by reference. The control device 100 still further can include an external connection element 118. Preferably, the external connection element 118 is positioned at the distal end 106 of the control device outer housing 102 and can be formed of a plurality of electrical connectors (118a, 118b, 118c). In one or more embodiments, the control device 100 may include a light source 139 that may comprise, for example, one or more light emitting diodes (LED) capable of providing one or more colors of lighting. The first light source 139 can be positioned directly on a printed circuit board (PCB) 141, and the PCB can include further control components (e.g., a microcontroller and/or memory components). An LED utilized as a light source as described herein may, for example, be selected of a design to emit light substantially upward from the plane of the PCB. Alternatively, or additionally, a suitable LED may include reflector elements adapted to or configured to emit light in a substantially different direction, such as parallel to the plane of the PCB, or at a desired angle that provides the desired result. As illustrated, the sensor 143 and the external connection element 118 are likewise directly attached to the PCB 141 or otherwise electrically connected to the PCB. The control device further can include electrical pins 120 positioned in the chamber 112 for forming an electrical connection with the cartridge 100 upon insertion of the cartridge into the chamber. As illustrated, the electrical pins 120 are positioned proximate a bottom portion of the chamber 112 and particularly may extend through a bottom wall 114a of the inner frame 114, which frame defines the boundaries of the chamber 112. One or more mechanical connectors 121 may also be present in the chamber 112, and particularly can be positioned in the inner frame 114, such as in the bottom wall 114a thereof. For example, mechanical connectors 121 can be magnetic elements (e.g., magnets or elements formed of material configured for forming a magnetic connection with a further magnet). Alternatively, the mechanical connectors 121 may be positioned in a side wall 114b of the inner frame 114 and thus may be configure for establishing a friction fit with the cartridge 200.

The control device outer housing 102 may be formed of any suitable material, such as a metal, plastic, ceramic, glass, or the like. Preferably, the control device inner frame 114 is formed of the same material as used to form the first device outer housing 102; however, different materials may be used. Although the control device inner frame 114 is illustrated as being a separate element from the control device outer housing 102, it is understood that, if desired, the inner frame may be defined by an internal surface of the outer housing and an added bottom plate (e.g., such that the bottom plate corresponds to the illustrated inner frame bottom wall 114*a*, and the internal surface of the outer housing corresponds to the illustrated inner frame side wall 114*b*).

As can be seen from the foregoing, the control device 100 can include a number of openings that provide opportunity for liquid contaminants to enter the control device outer housing 102. Accordingly, in some embodiments, the present disclosure can provide one or a combination of components adapted to or configured to reduce or prevent opportunity for liquid contaminants to enter the control device 100. By use of such component(s), the control device 100 can be adapted to or configured to be water resistant or waterproof. A control device 100 in particular can be provided with improved resistance to malfunction by configuring the control device to be resistant to infiltration of water through openings in the outer housing (e.g., seams where an end cap meets the outer housing, microperforations, openings for LED indicators, and the like), openings where electrical connectors are accessible, and the like). In particular, the presence of the light window 160 can provide a significant opening in the outer wall 104 of the outer housing 102 of the control device 100 that can allow for entry of liquid contaminants into the control device.

Example embodiments for achieving water resistance can be envisioned in relation to the configuration shown in FIG. 5. In some embodiments, water-resistance can be imparted by including sealing elements at various openings. For example, various measures may be employed to substantially prevent entry of liquids through the light window 160 formed on the outer wall 104 of the control device 100.

In one or more embodiments, the light guide 175 may be adapted to or configured to provide a sealing engagement with the outer wall 104 of the control device outer housing 102. For example, as illustrated in the embodiment shown in FIG. 6, a sealing member 177 may be positioned between the light guide 175 and the outer wall 104 of the control device outer housing 102. The sealing member 177 may be separate from the light guide 175 and, for example, may be a flexible gasket or similar element adapted to or configured to provide a substantially liquid resistive (e.g., water resistive) seal around substantially the entire periphery of the light window 160 (i.e., the sealing member being present substantially completely around the entire periphery of the light window). In some embodiments, the sealing member 177 may be integral to the light guide 175. Thus, the light guide 175 may be formed so as to integrally include the sealing member 177 and, as before, the sealing member may be adapted to or configured to provide a substantially liquid resistive seal around substantially the entire periphery of the light window 160. In such embodiments, the light guide 175 may effectively function as a seal/light diffuser and can be formed of a translucent elastomeric material such as silicone rubber, which provides both the waterproof seal as well as the light pipe effect for the LED.

In one or more embodiments, at least one sealing member can be included in the device in one or a plurality of locations to provide a water-proofing or water-resistant effect. Such sealing member may be comprised of an elastomeric material. In certain embodiments, such elastomeric material may be combined with and/or adhered to an end cap as further described herein. For example, such adhering can be carried out utilizing an over-molding or insert molding process. Such process may apply to any one or more sealing members that may be present according to the present disclosure.

In some embodiments, the transparent or translucent member 162 (see FIG. 2) can be adapted to or configured to function as a seal/light diffuser and can be, for example, a molded elastomeric component such as silicone rubber providing a seal in the light window 160. Such element may not be necessary when other elements are utilized. For example, the use of microperforations as described below may make it possible to forego the use of the transparent or translucent member 162 as a seal/light diffuser. Likewise, in embodiments wherein a selectively permeable venting material such as GORE-TEX® is utilized as a liquid-resistive member 180 and adhered to the inside surface of the control device 100 outer wall 104 in a location completely covering the light window 160, the seal/light diffuser 162 may not be utilized.

Implementation of a liquid-resistive member 180 according to example embodiments of the present disclosure is illustrated in FIG. 7, wherein the liquid resistive member 180 may be substantially in the form of a membrane, sheet, film, or the like that is substantially covering the light window 160. If desired, the liquid-resistive member 180 may be utilized in other portions of the control device 100 to improve the overall ability of the control device to resist infiltration by liquids. The liquid resistive member 180 may be, for example a GORE-TEX® membrane or similar material that is substantially water resistive or water-proof while also being breathable to allow passage of gases therethrough. The liquid resistive membrane 180 preferably is substantially permanently attached to the outer wall 104 of the control device outer housing 102 and, for example, may be glued, welded, or otherwise combined therewith. In some embodiments, the liquid resistive membrane 180 may be supplied with pressure sensitive adhesive on one side, with the adhesive in an outer area surrounding an inner area of no adhesive. This membrane achieves both venting and water-proofing to the standard desired. A separate light guide may still be required in this case in the location of the water resistive membrane 180. In this case the light guide need not be an elastomeric material, but could be a rigid plastic material more optimized for the light guide/diffuser function. Likewise, the light guide in such embodiments may also include particulate additives or be made from a more translucent polymer. In such cases, this can be effective to reflect/refract the light in a direction to exit the light window while attenuating the light as it moves down the length so as to create a diminishing brightness effect along the length of the slot. The liquid-resistive membrane 180 preferably can be sufficiently thin and translucent so as allow LED light transmission. In this case, the seal/light diffuser may be adapted to or configured to be only a light diffuser, which would allow use of optimized materials for light guide/diffusion, in place of the elastomer.

In some embodiments, a liquid-resistive membrane 180 may be adapted to or configured to function as all of a venting material, a water-resisting material, and a light guide material. For example, a translucent, selectively permeable material can be adhered to the inside surface of the control device outer shell 102 in a location completely covering the light window 160. The liquid-resistive membrane 180 may be supplied with pressure sensitive adhesive on one side as mentioned previously. In some embodiments, an expanded polytetrafluoroethylene (ePTFE) material may be used in the liquid-resistive membrane, and such materials are commonly available under the tradename GORE-TEX®. In some embodiments, a microporous polyurethane material may be used in the liquid-resistive membrane, and such materials are commonly available under the tradename Dermizax™. In some embodiments, the liquid-resistive membrane may comprise a multi-layer construction, such as including an outer layer treated with a durable water repellant (DWR), which can include a fluoropolymer, and also including an inner layer, which may include an ePTFE material, a microporous material, or other gas permeable and optional water-resistant material. Preferably, in such embodiments, the membrane material will exhibit optical properties that are tailored to properly diffuse the LED light for a desired "growing" effect while retaining the other needed physical properties. Similarly, in some embodiments the liquid-resistive membrane 180 may be significantly thicker. Instead of being adhered to the inner surface of the control device outer housing 102, the significantly thicker material may be adapted to or configured to substantially form a seal against the outer wall 104 over the light window 160 by being positioned in physical contact with the outer wall. This component thus can provide all three properties of light diffusion, waterproofing, and venting.

Returning to FIG. 5, in one or more embodiments, water resistance may be achieved at least in part through use of one or more O-rings 185, which can be used to substantially seal one or more sections of the control device 100. The O-ring 185 can be formed of an elastomeric material such as silicone rubber, and can be assembled, for example, in a groove 114c formed around an outer surface of the inner frame 114. This O-ring provides an air tight, water tight seal between the inner frame 114 and the outer wall 104 of the outer housing 102 of the control device 100.

In some embodiments, a sensor membrane/seal 187 can be included and can be a molded elastomeric (e.g., silicone rubber) component providing a seal between the electrical connectors 120 and the inner frame 114. The sensor membrane/seal 187 can be formed of a contact seal member 187a and, optionally, a pressure aperture seal 187b. The contact seal 187a will provide sealing around the electrical connectors 120 (e.g., forming a seal between the electrical connectors and the inner frame 114) while the pressure aperture seal 187b will provide sealing around the aperture(s) 115 utilized to allow air flow between the interior of the control device 100 and the interior of the inner frame 114 so pressure drop may be read when a user draws on a cartridge inserted into the inner frame. The design of this seal will not allow liquids or vapor to reach the pressure sensor and/or other internals of the control device 100 by passage around the electrical contact pins. As an alternative example alternate embodiment, the sensor/membrane seal may only form a seal around the pressure sensor, in which case additional separate discrete seals can be incorporated for the cartridge contact pins to waterproof the control device enclosure from those openings. These separate discrete seals may be insert molded or co-molded with the inner frame component of the control device. The pressure sensor 143 likewise may include a sensor seal 144 that partially surrounds the pressure sensor (see FIG. 4). The sensor seal 144 may be adapted to or configured to form an air seal around the pressure sensor 143 to improve sensitivity and ensure that the sensor is activated only when an actual pressure drop is caused by a use drawing on a cartridge that is inserted into the inner frame 114. As also illustrated in FIG. 5, the device may include a haptic motor 191 that may be at least partially surrounded by a rubber boot 193.

As further illustrated in FIG. 9, the sensor seal 144 may be adapted or configured to provide an isolated environment for at least the pressure sensor 143 on the PCB 141. In FIG. 9, the PCB 141 is positioned atop the battery 116 as opposed to being proximate the distal end 106 of the control device outer housing 102. In this example embodiment, a sensor seal 144 can be adapted to or configured to form a seal between the control device inner frame 114 and the PCB 141. This can be achieved, as illustrated, by forming a sensor seal 144 from one or a plurality of seal supports 146 and a flexible member 147 (e.g., a flexible membrane, diaphragm, or similar component) extending between the seal support(s) and over the pressure sensor. Preferably, the combination of elements forming the sensor seal 144 substantially completely surrounds and covers the pressure sensor 143. The seal support(s) 146 may extend fully between the PCB 141 and the control device inner frame 114 or may terminate short of contacting the inner frame. Although the flexible member 147 is positioned over the pressure sensor, such configuration is not limiting. Rather, any one or more components of the sensor seal 144 may be formed of such a flexible member. In particular, the sensor seal 144 may comprise an enclosure having at least one flexible surface.

Preferably, the sensor seal 144 is adapted to or configured to form an enclosed volume 148 around at least the pressure sensor 143 and, optionally, one or more further elements present on the PCB 141 (e.g., a haptic sensor, circuitry, or the like). The formation of such an enclosed volume 148 utilizing at least one flexible member can be effective to allow for movement and/or deflection of the flexible member in the presence of a pressure differential across the surface. This pressure differential may be created, for example, by a user's draw on the device so that a pressure change is transmitted through at least the aperture 115 into the control device outer housing 102. Because of the enclosed volume 148 formed by the sensor seal 144, the deflection of the flexible member 147 is efficiently transmitted to the pressure sensor 143 enclosed therein and allows the pressure sensor to detect the pressure differential caused by a user's draw on the device while maintaining a protective barrier against water and/or other liquids and/or aerosol and/or vapor that may be present.

The at least one flexible surface (e.g., flexible member 147) of the enclosure defining a sensor seal 144 may be in the form of a substantially thin section of elastomeric material that may be integrated into the sensor seal component. Alternatively, the at least one flexible surface may comprise such material that is separately attached to the sensor seal support(s) 146. The at least one flexible surface (e.g., the flexible member 147) may have a thickness of about 0.001 mm to about 0.3 mm, about 0.01 mm to about 0.2 mm, or about 0.05 mm to about 0.2 mm. In further embodiments, the at least one flexible surface may have a thickness of about 0.1 to about 0.3 mm. In some embodiments, the flexible member 147 or other flexible surface present on the sensor seal 144 may contain one or more geometric features such as corrugations and/or different areas having different thicknesses to assist or enhance the flexibility and/or increase the amount of movement or deflection of the surface in the presence of a pressure differential.

One or more materials forming a part of the sensor seal 144 may include a material that is adapted to or configured to substantially prevent the passage of water and/or other liquids and/or aerosol and/or vapor from outside of the enclosed volume 148 to inside of the enclosed volume, thereby protecting the components that are present within the enclosed volume from damage. In some embodiments, one or more materials forming a part of the sensor seal 144 may be formed from a selectively porous material that may be adapted to or configured to allow movement of air into and out of the enclosed volume 148 while substantially preventing the passage of water and/or other liquids.

The control device 100 may include an end cap 190 positioned in the distal end 106 of the control device outer housing 102. In some embodiments, a pin seal 192 can be included to provide a sealing arrangement between the external connection element(s) 118 and the bottom cap 190. The pin seal 192 can be a molded elastomeric component such as silicone rubber. As an alternative example embodiment, the pin seal can be a selectively permeable, flexible material instead of a waterproof elastomer. Examples include thicker versions of known selectively permeable materials made from polyolefins, polyesters, or Teflon-type materials. In this case, the pin seal would provide both waterproofing and venting in the same component.

In some embodiments, the bottom cap 190 may include a bottom cap O-ring 194, which can be an elastomeric material such as silicone rubber. The bottom cap O-ring 194 may be positioned in a groove 195 formed in the bottom cap 190. This O-ring provides a seal between the bottom cap 190 and the control device outer housing 102. Optionally the O-ring may be insert molded or may be combined via co-molded or over-molded processes with the bottom cap 190. This also may be implemented in relation to one or both of the O-ring 185 and the pin seal 192. All of these may be combined with the bottom cap 190 as desired using an over-molding process.

In some embodiments, a vent membrane as otherwise described herein can be inserted/adhered to the bottom cap 190, preferably to an interior surface thereof, and can be a selectively permeable material that provides permeability for air and vapor but does not allow water to pass up to the desired standard. Depending upon further materials being present, such vent membrane may not be required.

In some embodiments, a light window may not be required in order to provide visible lighting through the control device outer housing 102. As illustrated in FIG. 8, in some embodiments, a portion of the outer wall 104 of the outer housing 102 may be provided with a series of penetrations through the outer wall. More particularly, penetration in the outer wall 104 may comprise a series of micro-perforations 104'. The micro-perforations 104' may be adapted to or configured to provide a unique aesthetic effect with light passed through the light guide 175 from the light source 139, and the micro-perforations can also provide inherent water resistance to chosen standard. In particular, micro-perforations 104' can be sized to substantially slow passage of liquid therethrough such that prolonged contact with liquid would be required in order for the liquid to pass through the micro-perforations and into the interior of the control device 100. In some embodiments, the micro-perforations can have an average size (e.g., diameter) of about 40 µm to about 200 µm, about 50 µm to about 180 µm, or about 60 µm to about 150 µm. The series of micro-perforations may be positioned over a defined area of the control device outer housing 102, such as an area covering at least 5 mm², at least 10 mm², or at least 20 mm² (such as in the range of about 5 mm² to about 50 mm², about 5 mm² to about 40 mm², or about 5 mm² to about 25 mm²). The micro-perforations 104' may define a specific shape, such as an oval, a circle, a rectangle (or other parallelogram), or another geometric shape. In some embodiments, the micro-perforations may define a logo or other unique shape or design in the control device outer housing 102.

The foregoing disclosure encompasses multiple example embodiments by which the control device 100 may be substantially water-resistant or substantially water-proof. In particular, the use herein of the term "water-resistant" and/or "waterproof" can be intended to indicate that the device is thereby adapted to or configured to meet one or more standards set forth in one or more International Protection Marking Code, or IP Code. In certain embodiments, a water-resistant or waterproof device as described herein can be adapted to or configured to meet the IP67 requirements, and applicable IP Code requirements for being considered water-resistant or waterproof are incorporated herein by reference.

As seen in FIG. 4, a control device 100 according to the present disclosure can be adapted to or configured to be combined with a cartridge 200 to provide a functioning aerosol delivery system 10. A cartridge 200 for use in an aerosol delivery device 10 of the present disclosure can comprise a tank 201 that is defined by an outer tank wall 203 that includes a proximal end 205 and a distal end 207. One or more mating connectors 230 can be present at the distal end 207 of the cartridge 200 and can be configured to form a connection with the one or more mechanical connectors 121 present in the chamber 112 of the control device 100. The mating connectors 230, for example, can be magnetic elements (e.g., magnets or elements form of material configured for forming a magnetic connection with a further magnet). Alternatively, the mating connectors 230 may be present on one or more sides of the outer tank wall 203 and thus may be configured for establishing a friction fit with the chamber 112 of the control device 100.

The cartridge 200 is configured to contain a liquid composition for vaporization—i.e., an e-liquid or aerosol precursor composition, which may be configured as otherwise described herein. The tank 201 particularly can include an inner wall 202 that defines a reservoir 204 wherein the e-liquid or the like may be retained. An aerosol passage 212 can at least partially surround the reservoir 204 in a longitudinal direction from the distal end 207 to the proximal end 205 of the tank 201. In other embodiments, however, it is understood that the aerosol passage 212 may extend through at least a portion of the reservoir such that the reservoir is configured in an annular space between the aerosol passage and the outer tank wall 203.

The cartridge 200 further can comprise a mouthpiece 209 that is defined by an outer mouthpiece wall 211 that includes a proximal end 213 with an exit portal 215 and a distal end 217 that is engaging the proximal end 205 of the tank 201. Although the mouthpiece 209 is described as being a separate element from the tank 201, it is understood that the tank wall 203 may extend a greater distance so as to form an integral mouthpiece. As such, the mouthpiece may be attached to the tank, or the mouthpiece may be integrally formed with the tank. The cartridge 200 further can include a heater 219 and a liquid transport element 221 that defines a fluid connection between the heater and a liquid 223 contained within the reservoir 204. The heater 219 and liquid transport element 221 may be configured as separate elements that are fluidly connected or may be configured as a combined element. Moreover, the heater 219 and the liquid transport element 221 may be formed of any construction as otherwise described herein. The cartridge 200 also can include one or more electrical contacts 225 that are configured to electrically connect the heater 219 with the battery 116 in the control device 100 through contact with the electrical pins 120 when the cartridge is connected with the control device.

A liquid transport element 221 can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element). As further discussed herein, some embodiments of the present disclosure can particularly relate to the use of non-fibrous transport elements. As such, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some embodiments, a liquid transport element can be formed partially or completely from a porous monolith, such as a porous ceramic, a porous glass, or the like. Example monolithic materials suitable for use according to embodiments of the present disclosure are described, for example, in U.S. Pat. App. Ser. No. 14/988,109, filed Jan. 5, 2016, and US Pat. No. 2014/0123989 to LaMothe, the disclosures of which are incorporated herein by reference. The porous monolith can form a substantially solid wick.

Various embodiments of materials configured to produce heat when electrical current is applied therethrough may be employed to form the heater 219. As such, the battery 116 or other power source in the control device 100 and/or the control component 141 can be adapted to or configured to be connected with an atomizer, which may include a heater. In particular, the control component can be adapted to or configured to direct power at a variable level from the power source to the atomizer (e.g., the heater) in response to signaling received from the pressure sensor. In such manner, the control device can be adapted to or configured to provide adjustable lighting from the light source 139 based upon the power command received from the control component, which power command may correspond directly to the puff intensity on the device. For example, PWM, DAC, or any other means may be used to adjust the brightness of the light source.

In some embodiments, the heater can be a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further embodiments, the heater can be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater in particular may be configured to be substantially flat. Such heaters are described in U.S. Pat. Pub. No. 2016/0345633 to DePiano et al., which is incorporated herein by reference.

Further types of atomizer are also encompassed by the present disclosure. For example, in some embodiments, an atomizer may comprise one or more elements adapted to or configured vaporize or aerosolize (or otherwise form a fine, particulate form of) an aerosol precursor liquid without necessarily heating the liquid. For example, a piezo element may be used as a vaporizer in certain embodiments of the present disclosure, and suitable piezo elements are described, for example, in U.S. Pat. Pub. No. 2013/0319404 to Feriani et al. and U.S. Pat. Pub. No. 2019/0014819 to Sur, the disclosures of which are incorporate herein by reference.

The outer tank wall 203 can be configured to be at least partially transparent or translucent so that the liquid 223 contained therein is visible externally. As such, the entire outer tank wall 203 can be transparent or translucent. Alternatively, only a single side of the outer tank wall 203 can be transparent or translucent while the remaining portions of the outer tank wall can be substantially opaque. In further embodiments, the outer tank wall 203 can be colored. The aerosol delivery device 10 can be configured in some embodiments so that at least a portion of the tank 201 is visible when the cartridge 200 is engaged with the control device 100. Likewise, at least a portion of the inner wall 202 that defines the reservoir 204 can be transparent or translucent. In one or more embodiments, the outer wall 104 of the control device 100 can be configured to include a window through which the outer tank wall 203 and optionally any liquid 223 present in the tank 201 (or specifically in the reservoir 204) can be visible when the cartridge 200 is engaged with the control device 100. As seen in FIG. 1, a window 135 is configured as a cut-out in the outer wall 104 of the control device 100 that is positioned near the proximal end 108 of the control device. The window 135 preferably is positioned to provide visual access into the chamber 112 of the control device 100. As illustrated, the cut-out is substantially oval-shaped; however, it is understood that any shape is encompassed herein. In some embodiments, the window 135 may be configured as a notch extending from the proximal end 108 of the outer wall 104 of the control device 100 a distance toward the distal end 106 of the control device. In other embodiments, the window 135 may be configured to not have any open borders and thus may expressly exclude a notch configuration as noted above. In certain embodiments, a window 135 may be expressly excluded from the control device 100. Moreover, the window 135 may be completely open or the window may have a transparent member (e.g., glass or plastic) positioned in the opening defined by the window or covering the window on one or both of the inner surface and outer surface of the outer wall 104 of the control device 100.

The aerosol delivery device 10 most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

In use, when a cartridge 200 is inserted into the chamber 112 of the control device 100, the fit may be such that air is capable of passing between the outer surface of the tank wall 203 and the inner surface of the inner frame 112 of the control device. Thus, when a user puffs on the mouthpiece 209 air may pass between the outer surface of the tank wall 203 and the inner surface of the inner frame 112, pass through an air entry 220 in the cartridge 200, mingle with formed vapor near the heater 219, pass through the aerosol passage 212, and ultimately pass through the exit portal 215. The passage of air as defined above may be effective to cause pressure drop in the control device 100 that can be sensed by the sensor 143 through the aperture 115.

An input element may be included with the aerosol delivery device (and may replace or supplement an airflow or pressure sensor). The input may be included to allow a user to control functions of the device and/or for output of information to a user. Any component or combination of components may be utilized as an input for controlling the function of the control device 100. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included, choosing the total particulate matter (TPM) provided per puff, choosing a specific heating profile to be implemented, choosing a modifiable resistance to drawn, and the like.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator. Likewise, a flow sensor may be replaced with a manual actuator, such as a push button.

In one or more embodiments, the present disclosure may be directed to kits that provide a variety of components as described herein. For example, a kit may comprise a control device with one or more cartridges. A kit may further comprise a control device with one or more charging components. A kit may further comprise a control device with one or more batteries. A kit may further comprise a control device with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control devices may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
   at least one wall defining an outer housing;
   a window in the at least one wall, the window extending between a first end and a second end;
   a light source positioned within the outer housing and being connectable to a power source; and
   a control component configured to direct power at a variable level from the power source to the light source such that light emitted from the light source fills a quantity of the window, the quantity corresponding to the variable level of power delivered to the light source.

2. The aerosol delivery device of claim 1, wherein the light source is offset from the window so as to be beyond one of the first end of the window and the second end of the window.

3. The aerosol delivery device of claim 1, further comprising a light guide positioned within the outer housing and proximate the window, the light guide being of sufficient size to substantially fill the window and at least partially overlap with the light source, wherein the light emitted from the light source is transmitted through the light guide and fills the quantity of the window.

4. The aerosol delivery device of claim 3, wherein the position of the light source and the position of the light guide is effective to achieve the light emitted from the light source and transmitted through the light guide to grow in a direction from one of the first end of the window and the second end of the window to the other of the first end of the window and the second end of the window as power delivered from the power source to the light source increases and to recede in reverse of the direction as power delivered from the power source to the light source decreases.

5. The aerosol delivery device of claim 1, further including a pressure sensor configured to detect changes in pressure within the outer housing across a continuous pressure intensity range and provide signaling to the controller corresponding to the pressure intensity.

6. The aerosol delivery device of claim 5, wherein the control component is configured to adjust the variable level of the power delivered from the power source to the light source in response to the signaling received from the pressure sensor.

7. The aerosol delivery device of claim 5, wherein the power source and the control component are configured for connection with an atomizer.

8. The aerosol delivery device of claim 7, wherein the control component is configured to direct power at a variable level from the power source to the atomizer in response to the signaling received from the pressure sensor.

9. The aerosol delivery device of claim 1, further comprising a printed circuit board positioned within the outer housing, the light source being positioned on the printed circuit board.

10. The aerosol delivery device of claim 9, wherein the control component is positioned on the same printed circuit board as the light source.

11. The aerosol delivery device of claim 3, further comprising a sealing member positioned between the light guide and the at least one wall defining the outer housing.

12. The aerosol delivery device of claim 11, wherein the sealing member is integral with the light guide.

13. The aerosol delivery device of claim 12, wherein the light guide is formed of a translucent elastomeric material.

14. The aerosol delivery device of claim 1, further comprising a liquid-resistive membrane positioned interior to the outer housing, the liquid-resistive membrane covering the window in the at least one wall.

15. The aerosol delivery device of claim 14, wherein the liquid-resistive membrane is adhered to an interior surface of the at least one wall.

* * * * *